US012601748B2

(12) United States Patent
Sanchez

(10) Patent No.: US 12,601,748 B2
(45) Date of Patent: Apr. 14, 2026

(54) PROSPECTIVE MARKERS IN TRAUMATIC BRAIN INJURY (TBI)

(71) Applicant: UNIVERSITE DE GENEVE, Geneva (CH)

(72) Inventor: Jean-Charles Sanchez, Chêne-Bourg (CH)

(73) Assignee: UNIVERSITE DE GENEVE, Geneva (CH)

( * ) Notice: Subject to any disclaimer, the term of this patent is extended or adjusted under 35 U.S.C. 154(b) by 950 days.

(21) Appl. No.: 17/426,646

(22) PCT Filed: Jan. 30, 2020

(86) PCT No.: PCT/EP2020/052307
§ 371 (c)(1),
(2) Date: Jul. 29, 2021

(87) PCT Pub. No.: WO2020/157206
PCT Pub. Date: Aug. 6, 2020

(65) Prior Publication Data
US 2022/0120766 A1      Apr. 21, 2022

(30) Foreign Application Priority Data
Jan. 31, 2019    (EP) ..................................... 19154845

(51) Int. Cl.
*G01N 33/68*        (2006.01)
*G01N 33/563*       (2006.01)

(52) U.S. Cl.
CPC ....... *G01N 33/6896* (2013.01); *G01N 33/563* (2013.01); *G01N 2800/28* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2009/0325920 A1 * | 12/2009 | Hoffman ................ | A61K 31/57 |
| | | | 514/177 |
| 2014/0303041 A1 | 10/2014 | Hayes et al. | |
| 2015/0030609 A1 * | 1/2015 | Mohapatra ........... | C12Q 1/6883 |
| | | | 435/7.1 |
| 2017/0003303 A1 | 1/2017 | Keane et al. | |
| 2018/0238907 A1 | 8/2018 | Sanchez et al. | |
| 2020/0110100 A1 | 4/2020 | Sanchez et al. | |

FOREIGN PATENT DOCUMENTS

| | | | | |
|---|---|---|---|---|
| WO | WO-2016055148 A2 * | 4/2016 | ......... | G01N 33/6896 |
| WO | 2018228927 A1 | 12/2018 | | |
| WO | WO-2018222783 A1 * | 12/2018 | ........... | A61B 5/4064 |

OTHER PUBLICATIONS

Poovindran, AR. "Traumatic Brain Injury: Studies on Serum Biomarkers for Diagnosis and Single Nucleotide Polymorphisms to Predict Outcome" ProQuest Dissertations & Theses. (2015) (Year: 2015).*
Gill J. et al. "Higher exosomal tau, amyloid-beta 42 and IL-10 are associated with mild TBIs and chronic symptoms in military personnel", Brain Inj. 2018;32(10):1277-1284. (Year: 2018).*
Singh K et al., "Longitudinal changes in the DTI measures, anti-GFAP expression and levels of serum inflammatory cytokines following mild traumatic brain injury", Exp Neurol. Jan. 2016:275 Pt 3:427-435 (Year: 2016).*
Kochanek PM et al. "Screening of Biochemical and Molecular Mechanisms of Secondary Injury and Repair in the Brain after Experimental Blast-Induced Traumatic Brain Injury in Rats", J Neurotrauma. Jun. 1, 2013;30(11):920-37. (Year: 2013).*
Written Opinion of the International Application No. PCT/EP2020/052307, Apr. 22, 2020, 9 pages.
Hossain Iftakher, et al., "Early Levels of Glial Fibrillary Acidic Protein and Neurofilament Light Protein in Predicting the Outcome of Mild Traumatic Brain Injury, Journalofneurotrauma.", vol. 36, No. 10, Jan. 8, 2019, pp. 1551-1560.
Lagerstedt, Linnea , et al., "Combining H-FABP and GFAP increases the capacity to differentiate between CT-positive and CT-negative patients with mild traumatic brain injury, Plos One", pp. 1-13, Jul. 9, 2018.
Schneider Soares, Mahatma Flávia, et al., "Interleukin-10 is an Independent Biomarker of Severe Traumatic Brain Injury Prognosis, Neuroimmunomodulation", vol. 19, No. 6, Jan. 1, 2012, pp. 377-385.
Vos, P. E, et al., "Glial and neuronal proteins in serum predict outcome after severe traumatic brain injury", Neurology, vol. 62, No. 8, Apr. 27, 2004, pp. 1303-1310.
Waldner Bernhard, et al., "The Prognostic Significance of the Serum Biomarker Heart-Fatty Acidic Binding Protein in Comparison with S100b in Severe Traumatic Brain Injury, Journalofneurotrauma.", vol. 30, No. 19, Oct. 1, 2013, pp. 1631-1637.
Mälarstig, et al., "Raised interleukin-10 is an indicator of poor outcome and enhanced systemic inflammation in patients with acute coronary syndrome", Heart, vol. 94, 2008, pp. 724-729.

* cited by examiner

*Primary Examiner* — Daniel E Kolker
*Assistant Examiner* — Peter Johansen
(74) *Attorney, Agent, or Firm* — Synergy IP Group AG; Lily Ackerman

(57) ABSTRACT

The invention provides an in vitro prospective method for determining a recovery outcome in one or more samples of a subject having experienced traumatic brain injury (TBI), comprising the steps of a) determining the level of at least one biomarker selected from the group consisting of H-FABP, IL-10, GFAP, NF-L and S100B; and b) comparing each level obtained under step a) with a corresponding reference value to determine the recovery outcome. The invention also provides a device comprising an assay for determining a recovering outcome in one or more samples of a subject having experienced traumatic brain injury (TBI), the assay comprising means for detecting the level of at least one biomarker selected from the group consisting of H-FABP, IL-10, GFAP, NF-L and S100B.

11 Claims, No Drawings

PROSPECTIVE MARKERS IN TRAUMATIC BRAIN INJURY (TBI)

CROSS REFERENCE TO RELATED APPLICATIONS

This application is a United States National Stage Application filed under 35 U.S.C. § 371 claiming the benefit of PCT Application No. PCT/EP2020/052307, filed on Jan. 30, 2020, which claims priority to and the benefit of European Application No. 19154845.2, filed on Jan. 31, 2019, all of which are incorporated herein by reference in their entireties.

BACKGROUND OF THE INVENTION

The invention relates to methods and devices for the prediction of the outcome of brain or brain related injuries, particularly traumatic brain injury (TBI). The invention also relates to treatments following such injuries.

Traumatic brain injury (TBI) is a major health problem worldwide with a high death- and disability rate. Patients having experienced a TBI may suffer from different levels and persistence of cognitive, behavior, emotional and physical impairments. This may further affect the patient quality of life through difficulties to perform daily activities, work and social life. Different biomarkers have been suggested as outcome indicator to increase the clinician prediction capacities with the objective to improve and optimize patients care-taking. To date, most known biomarkers tend to have low prediction capacities and therefore are not suitable for clinical use.

Thus, there remains a need to provide predictive biomarkers-based methods and tests relating to the TBI outcome in patients and which help to facilitate and simplify treatment in a cost-effective way.

Hence, one object underlying the present invention is to provide biomarkers-based methods and tests useful for the prediction of disease outcome in a patient who has experienced traumatic brain injury (TBI).

Another object underlying the present application is to provide biomarkers-based methods and tests useful for the prediction of the recovery in a patient who has experienced traumatic brain injury (TBI).

SUMMARY OF THE INVENTION

In a first aspect, the invention relates to an in vitro prospective method for determining a recovery outcome in one or more samples of a subject having experienced traumatic brain injury (TBI), comprising the steps of
a) determining the level of at least one biomarker selected from the group consisting of H-FABP, IL-10, GFAP, NF-L and S100B;
b) comparing each level obtained under step a) with a corresponding reference value to determine the recovery outcome.

In a further aspect, the present invention provides a device comprising an assay for determining a recovering outcome in one or more samples of a subject having experienced traumatic brain injury (TBI), the assay comprising means for detecting the level of at least one biomarker selected from the group consisting of H-FABP, IL-10, GFAP, NF-L.

In yet a further aspect, the invention provides for a method for treating a subject having experienced traumatic brain injury (TBI) comprising the steps of:

a) performing the in vitro prospective method described above.
b) treating the subject having an unfavorable outcome under step a) with a neuroprotective agent.

In yet a further aspect, the invention relates to a neuroprotective agent for use in treating a subject having experienced traumatic brain injury (TBI) and having an unfavorable recovery outcome in accordance with the in vitro prospective method described above.

DETAILED DESCRIPTION OF THE INVENTION

In a first aspect, the invention relates to an in vitro prospective method for determining a recovery outcome in one or more samples of a subject having experienced traumatic brain injury (TBI), comprising the steps of
a) determining the level of at least one biomarker selected from the group consisting of H-FABP, IL-10, GFAP, NF-L and S100B;
b) comparing each level obtained under step a) with a corresponding reference value to determine the recovery outcome.

In the following, the invention, and certain terms which are used to define it, will be described in more detail.

"Brain injury" is any state of a patient or individual which is the cause of sudden impact on the head or the individual. A particular brain injury is traumatic brain injury, i.e. TBI.

"TBI" in the sense of the invention is any brain injury caused by a traumatic incident.

"Identification" or "identify" or "classify" in the sense of the invention is the analysis of one or more samples of an individual to assess the possible outcome of said individual after brain injury and particularly TBI.

A "predictive" or "prospective" method in the sense of the invention is a method useful in providing information on a future development of a patient or individuum or subject who has been subject to a certain experienced or an impact or a shock or a traumatic incident, e.g. a brain injury, and in particular the recovery of said subject from said brain injury after a defined time span; said time span may be 1, 2, 3, 4, 5, or 6 months, or 1 or 2 years.

"Diagnostic method" or "diagnostic" in the sense of the invention is any useful method with a suitable sequence of method steps for the detection, visualization and/or quantification of the test result generally known in the art.

"Assay" in the sense of the invention is any method generally known in the art to detect the level of one or more of the above biomarkers for the TBI prediction outcome, like ELISA, lateral-flow assay, mass spectrometry, size-exclusion chromatography, western-blot or any other standard methods for detection of biomarkers.

"Device" in the sense of the invention is an apparatus, a kit or a system comprising an assay as described above. Examples are carrier plates, test stripes, biochip arrays or the like known in the art.

"Marker" or "biomarker" or "molecular marker" or "molecular biomarker" in the sense of the invention is any marker, such as a protein biomarker, which is described above, alone or in combination. The detection level of such marker in one or more samples enables to predict the brain injury outcome, preferably the traumatic brain injury (TBI) and/or other disorders as described below; the marker is detected by means of one or more assays as described above.

The at least one biomarker in step a) of the method according to the invention is heart-type fatty acid binding protein (H-FABP), interleukin 10 (IL-10), glial fibrillary acidic protein (GFAP), neurofilament protein (NF-L), S 100 calcium-binding protein B (S100B), combinations of two or three thereof.

In an embodiment, the at least one biomarker is H-FABP, IL-10, GFAP, NF-L and S100B, combinations of two or three thereof.

In another embodiment, the at least one biomarker is IL-10 and S100B, IL-10, H-FABP and S100B, IL-10 and H-FABP, IL-10, H-FABP and GFAP, H-FABP, GFAP and S100B, or H-FABP and GFAP, H-FABP and NF-L, H-FABP, GFAP and NF-L.

In another embodiment, the at least one biomarker in step a) is any combination of H-FABP, IL-10, GFAP, NF-L and S100B. In yet another embodiment, the least one biomarker in step a) cannot be further combined with any other protein marker In another embodiment, additional biomarkers can be added to the at least one biomarker described above.

It could be shown that a combination in the method of two markers can increase the accuracy for favorable outcome and/or complete recovery prediction.

The use of the above markers and in particular a combination of two or more markers showed very good results and increased accuracy of predictability of outcome.

The level of the at least one biomarker described above may be optionally combined with additional patient and/or clinical parameters including age, sex, Glasgow Coma Scale (GCS), Glasgow Outcome Scale (GOS) score, GOS extended (GOSE) score, Marshall score, Abbreviated Injury Score (AIS) and Injury Severity Score (ISS), and/or with one or more results from other diagnostic methods comprising Computerized Tomography (CT) scan and Magnetic Resonance Imaging (MRI). These additional patient parameters and results from other diagnostic methods can likewise be considered as "markers" in the sense of the invention.

In one embodiment, the at least one biomarker is combined with age, Marshall score, ISS and/or GCS.

In another embodiment, the level of the at least one biomarker can be combined with age or GCS score.

Markers like age and GCS can also be used in the sense of the invention to define a patient subgroup or subgroup of individuals. A preferred age group is below 50, 60, 70 or more than 50, 60, 65, 70 years of age. A GCS of 3 to 8, 9 to 12 and 13 to 15 can preferably be used to define a patient subgroup and can be used in combination with any of the other markers defined herein. In such a manner the individuals can be stratified and patient groups can be formed both to adapt and increase the test performance or to reduce the markers needed to achieve a reliable test result and preferably to adjust the features of the detection method or the components of a test kit.

"Severity" can be classified using an aggregate covariate combining the lowest Glasgow Coma Scale (GCS) before possible intubation and the length of posttraumatic amnesia.

A marker "panel" in the sense of the invention is a combination of at least two markers, such as two or three markers, whose detected levels, values or scores are used in combination for determining a recovery outcome of a subject having experienced traumatic brain injury (TBI).

"Sensitivity" in the sense of the invention refers to the assay result of true positives in the analysis of TBI. In one embodiment, the sensitivity in the analysis according to the invention is set to 95% to 100%, or 100% (i.e. no false negative diagnoses).

"Specificity" in the sense of the invention is the so-called true negative rate in an assay to identify TBI. In one embodiment, the specificity is targeted to be at least 50% and preferably higher, e.g. 58%, 60%, 65%, 70%.

In an embodiment, the sensitivity and specificity in the method as described herein will vary depending on the combination of the method parameters. In an embodiment, the method is characterized by a sensitivity of more than 90%, more than 95%, 96% or 97% or of 100%, and a specificity of more than 40%, or at least 50%, or a sensitivity of more than 95% and a specificity of at least 25%, or 28%, or 36%.

In yet a further embodiment, the specificity is set to more than 90, 95%, 96% or 97% or 100% (i.e. no false positive diagnoses) and the sensitivity is targeted to be at least 50% and preferably higher, e.g. 58%, 60%, 65%, 70%.

A "sample" or "specimen" in the sense of the invention is any fluid or tissue sample taken from a patient having experienced brain injuries, which fluid or tissue is useful for performing an assay or detection method to determine a recovery outcome in such patient. Preferably the sample is blood, plasma, urine, saliva, tears (lachrymal fluid) or cerebrospinal fluid (CSF). In an embodiment, the sample is blood. The sample is treated according to generally known procedures to keep or make them feasible for the marker analysis according to the invention.

A "Glasgow Outcome Scale Extended" (GOSE) in the sense of the invention is a read out of a method wherein the GOSE read out is divided into groups of GOSE equal or greater than 5 (favorable outcome), GOSE equal or less than 4 (unfavorable outcome), GOSE is equal to essentially 8 (complete recovery), and GOSE is equal to or less than 7 (incomplete recovery). In an embodiment, the recovery outcome is assessed in accordance with the in vitro prospective method of the present invention by means of the GOSE.

A "threshold" or a "panel cut-off" is defined for each biomarker by an optimization procedure defined in the following sections. A patient score is the number of biomarkers exceeding their threshold values. It can be defined as:

$$S_p = \sum_{i=1}^{n} I(X_{ip} \ge T_i)$$

where Sp is the score for patient p, n is the number of biomarkers, Xip is the concentration of the ith biomarker in patient p, Ti is the threshold for the ith biomarker, and l(x) is an indicator function which takes the value of 1 for x=true and 0 otherwise. If biomarker concentrations are higher in the control than in the disease group, then they are multiplied by −1 before applying the previous formula. To classify a patient, a threshold on the Sp score is required and defined as Ts. Patients with a score Sp≥Ts are positive; negative otherwise.

Marshall Classification of Traumatic Brain Injury (Marshall Score)

The "Marshall classification of traumatic brain injury" is a CT scan derived metric using only a few features and has been shown to predict outcome in patients with traumatic brain injury, Classification diffuse injury I (no visible pathology)

no visible intracranial pathology diffuse injury II midline shift of 0 to 5 mm basal cisterns remain visible no high or mixed density lesions>25 cm$^3$ diffuse injury III (swelling)

midline shift of 0 to 5 mm basal cisterns compressed or completely effaced no high or mixed density lesions>25 cm$^3$ diffuse injury IV (shift)

midline shift>5 mm no high or mixed density lesions>25 cm$^3$ evacuated mass lesion V any lesion evacuated surgically non-evacuated mass lesion VI high or mixed density lesions>25 cm$^3$ not surgically evacuated Abbreviated Injury Scale (AIS)

The Abbreviated Injury Scale (AIS) is an anatomically based consensus-derived global severity scoring system that classifies each injury in every region of the body according to its relative severity on a six-point ordinal scale:

1. Minor
2. Moderate
3. Serious
4. Severe
5. Critical
6. Maximal (currently untreatable).

There are nine AIS chapters corresponding to nine body regions:

1. Head
2. Face
3. Neck
4. Thorax
5. Abdomen
6. Spine
7. Upper Extremity
8. Lower Extremity
9. External and other.

Injury Severity Score

The Injury Severity Score (ISS) is based upon the AIS. To calculate an ISS for an injured person, the body is divided into six ISS body regions. These body regions are:

1. Head or neck—including cervical spine
2. Face—including the facial skeleton, nose, mouth, eyes and ears
3. Chest—thoracic spine and diaphragm
4. Abdomen or pelvic contents—abdominal organs and lumbar spine
5. Extremities or pelvic girdle—pelvic skeleton
6. External (unsurvivable)

To calculate an ISS, take the highest AIS severity code in each of the three most severely injured ISS body regions, square each AIS code and add the three squared numbers for an ISS (ISS=A$^2$+B$^2$+C$^2$ where A, B, C are the AIS scores of the three most injured ISS body regions). The ISS scores range from 1 to 75 (i.e. AIS scores of 5 for each category). If any of the three scores is a 6, the score is automatically set at 75. Since a score of 6 ("unsurvivable") indicates the futility of further medical care in preserving life, this may mean a cessation of further care in triage for a patient with a score of 6 in any category.

In the method according to the present invention, different time points may be used and defined wherein the method can be performed on one or more samples taken, independently, less than 24 hours, 1, 2, 3 and/or 6 months after occurrence of TBI.

According to an embodiment of the present invention, the level of the at least one marker can be determined in the same sample at different time points. In case the level of two or more markers is determined, it is also possible to use different samples for different markers, the sample being taken either at the same or at a different moment in time.

The method according to the present invention may also make use of an algorithm to calculate the recovery outcome from the detected levels, values or scores of the combination of at least two markers, such as two or three markers.

In a further aspect, the present invention relates to a device comprising an assay for determining a recovering outcome in one or more samples of a subject having experienced traumatic brain injury (TBI), the assay comprising means for detecting the level of at least one biomarker selected from the group consisting of H-FABP, IL-10, GFAP, NF-L and S100B.

In an embodiment, the at least one biomarker is H-FABP, IL-10, GFAP, NF-L and S100B, combinations of two or three thereof.

In yet another embodiment, the at least one biomarker is IL-10 and S100B, IL-10, H-FABP and S100B, IL-10 and H-FABP, IL-10, H-FABP and GFAP, H-FABP, GFAP and S100B, H-FABP and GFAP, H-FABP and NF-1, H-FABP, GFAP and NF-1.

In another embodiment, the at least one biomarker is any combination of H-FABP, IL-10, GFAP, NF-L and S100B.

In case of two or more markers, it is also possible to use a different device for each different marker, by using the same or different samples, at the same or at a different moment in time.

According to a further embodiment of the present invention, the means for detecting the level of at least one biomarker is an antibody.

In another embodiment, the device further comprises means for comparing the level of the at least one biomarker with a corresponding reference value to determine the recovery outcome.

The assay device will comprise and use components as known to the skilled person and hence do not need to be described in all detail here. Such an assay device may comprise or consist of a biochip, biomarker panel, a carrier, or a test strip and optionally comprise additional components or/and may be combined with additional components and software as is useful.

In yet another aspect, the disclosure relates to a method for stratifying individuals for the treatment of TBI using a method and a device as described above.

In yet another aspect, the disclosure relates to a method for treating a subject having experienced traumatic brain injury (TBI) comprising the steps of: a) performing a method as described above; b) treating the subject having an unfavorable outcome under step a) with a neuroprotective agent. In an embodiment, the neuroprotective agent comprises AC-11, acetyl-L-carnitine, acetylcholinerase inhibitors, acetylcysteine, an anti-protein-aggregation agent, simvastatin, growth hormone, rosuvastatin, statins, marijuana, β-blockers, enzogenol, cerebrolysin, nitric oxide synthase inhibitor, progesterone, ethanol, barbiturates, erythropoietin, hypothermia.

In an embodiment, the unfavorable outcome under step a) is assessed by a score of four (4) or less in accordance with the Glasgow Outcome Scale Extended (GOSE). In yet another aspect, the disclosure relates to a neuroprotective agent for use in treating a subject having experienced traumatic brain injury (TBI) and said subject having an unfavorable recovery outcome in accordance with the in vitro prospective method described above. In an embodiment, the neuroprotective agent comprises AC-11, acetyl-L-carnitine, acetylcholinerase inhibitors, acetylcysteine, an anti-protein-aggregation agent, simvastatin, growth hormone, rosuvastatin, statins, marijuana, β-blockers, enzogenol, cerebrolysin, nitric oxide synthase inhibitor, progesterone, ethanol, barbiturates, erythropoietin, hypothermia. In another embodiment, the unfavorable outcome is assessed by a score of four (4) or less in accordance with the Glasgow Outcome Scale Extended (GOSE).

The following list of numbered items are embodiments comprised by the present invention:

1. A prospective method for determining the recovery outcome in a sample of a subject having experienced traumatic brain injury (TBI) comprising the steps of using a sample of said subject under suitable conditions and detecting at least one biomarker under suitable conditions wherein the biomarker is selected from the group consisting of H-FABP, IL-10, S100B, GFAP and NF-L or fragments thereof, preferably two or three biomarkers are combined, more preferably IL-10 and H-FABP, or H-FABP and GFAP, or IL-10, H-FABP and GFAP, or any of IL-10, H-FABP, NSE, GAP43, NFH, NFM, Tau and S100B are combined, optionally combined with age, sex, GCS, CT scan or/and MRI results, Marshall score, injury score (AIS), the injury severity score (ISS).

2. Method according to item 1 wherein the read out predicts the Glasgow Outcome Scale Extended (GOSE) score.

3. Method according to item 2 wherein the GOSE read out is divided into groups of GOSE equal or greater than 5 (favorable outcome), GOSE equal or less than 4 (unfavorable outcome), GOSE is equal to essentially 8 (complete recovery), and GOSE is equal to or less than 7 (incomplete recovery).

4. Method according to items 1, 2 or 3 wherein the sample is blood, plasma, urine, saliva, tears (lachrymal fluid), or CSF.

5. Method according to item 1, 2, 3 or 4 wherein the method is performed less than 24 h, 1, 2, 3 or/and 6 months after occurrence of TBI.

6. Method according to any of the preceding items wherein the method is characterized by a sensitivity of more than 90%, more than 95%, 96% or 97% and a specificity of more than 40%, or at least 50%, or a sensitivity of more than 95% and a specificity of at least 25%, or 28%, or 36%.

7. Composition comprising or consisting of at least one or more markers useful prospective method for determining the recovery outcome in a sample of a subject having experienced traumatic brain injury (TBI) wherein the markers are selected from the group consisting of H-FABP, IL-10, S100B, GFAP and NF-L or fragments thereof, preferably a combination of IL-10 and H-FABP, or H-FABP and GFAP, or IL-10, H-FABP and GFAP, or any of IL-10, H-FABP, NSE, GAP43, NFH, NFM, Tau and S100B are combined, optionally combined with age, sex, GCS, CT scan or/and MRI results, Marshall score, injury score (AIS), the injury severity score (ISS).

8. Kit comprising or consisting of one or more markers according to item 7.

9. Assay device comprising one or more markers according to item 1.

10. Assay device according to item 9 which device comprises or consists of a biochip, biomarker panel, a carrier, or a test strip.

11. A method according to item 1, which makes use of an algorithm.

12. A method for stratifying individuals for the treatment of TBI using a method according to any of items 1 to 6, a composition according to item 7, a kit according to item 8, an assay device according to items 9-10 or/and an algorithm according to item 11.

13. A method for treating a subject having experienced traumatic brain injury (TBI) comprising the steps of: a.) performing a method according to any of items 1 to 6; b.) treating the subject with a GOSE score of 4 or less with a neuroprotective agent, preferably selected from the group consisting of AC-11, Acetyl-L-carnitine, Acetylcholinerase inhibitors, Acetylcysteine, an anti-protein-aggregation agent, and simvastatin, growth hormone, rosuvastatin, statins, marijuana, β-blockers, enzogenol, cerebrolysin, Nitric Oxide, Synthase Inhibitor, progesterone, ethanol, barbiturates, erythropoietin, hypothermia, 14. A neuroprotective agent, preferably selected from the group consisting of AC-11, Acetyl-L-carnitine, Acetylcholinerase inhibitors, Acetylcysteine, an anti-protein-aggregation agent, simvastatin, growth hormone, rosuvastatin, statins, marijuana, β-blockers, enzogenol, cerebrolysin, Nitric Oxide Synthase Inhibitor, progesterone, ethanol, barbiturates, erythropoietin, hypothermia or others for use in treating a subject having experienced traumatic brain injury (TBI) and said subject having been diagnosed with a GOSE score of 4 or less according to a method of any items 1 to 6.

The following examples serve to illustrate the invention. However, they should not be understood as restricting the scope of the invention.

EXAMPLES

1. Study Population

A total of 88 TBI patients with blood samples available within 24 hours from the time of injury were recruited to this study of which 69% were male. The most common causes of trauma were falls and traffic accidents. The distribution of severity, imaging findings, and outcome are shown in Table 1

TABLE 1

| | TBI patients' characteristics | | | | | | | |
| --- | --- | --- | --- | --- | --- | --- | --- |
| | TBI all severities | | | | Mild TBI | | | |
| | Complete recovery | | Favorable outcome | | Complete recovery | | Favorable outcome | |
| | GOSE 8 (n = 25) | GOSE 1-7 (n = 63) | GOSE 5-8 (n = 60) | GOSE 1-4 (n = 28) | GOSE 8 (n = 25) | GOSE 1-7 (n = 24) | GOSE 5-8 (n = 45) | GOSE 1-4 (n = 4) |
| Age | | | | | | | | |
| Mean (SD*) | 40.9 (20.27) | 51.13 (18.39) | 44 (18.68) | 57.25 (18.02) | 40.9 (20.3) | 47.5 (18.7) | 43.4 (19.6) | 52.8 (20.9) |
| Gender | | | | | | | | |
| Male, n (%) | 17 (68) | 44 (69.8) | 43 (71.7) | 18 (64.3) | 17 (68) | 9 (37.5) | 31 (68.9) | 1 (25) |
| Marshall Score n (%) | | | | | | | | |
| No visual pathology (Grade 1) | 17 (68) | 18 (28.6) | 33 (55) | 2 (7.1) | 17 (68) | 11 (45.8) | 28 (62.3) | |
| Diffuse injury (Grade 2) | 4 (16) | 11 (17.5) | 11 (18.3) | 4 (14.3) | 4 (16) | 9 (37.5) | 10 (22.2) | 3 (75) |
| Diffuse injury with swelling (Grade 3) | 0 (0) | 1 (1.6) | 0 (0) | 1 (3.6) | 0 (0) | 0 (0) | — | — |
| Diffuse injury with shift (Grade 4) | 0 (0) | 0 (0) | 0 (0) | 0 (0) | 0 (0) | 0 (0) | — | — |
| Evacuated mass lesion (Grade 5) | 1 (4) | 22 (34.9) | 9 (15) | 14 (50) | 1 (4) | 1 (4.2) | 2 (4.4) | — |
| Non evacuated mass lesion (Grade 6) | 3 (12) | 11 (17.5) | 7 (11.7) | 7 (25) | 3 (12) | 3 (12.5) | 5 (11.1) | 1 (25) |
| Injury Severity Score (ISS), n (%) | | | | | | | | |
| Minor 1-8 | 16 (64) | 13 (20.6) | 27 (45) | 2 (7.1) | 16 (64) | 10 (41.7) | 25 (55.6) | 1 (25) |
| Moderate 9-15 | 4 (16) | 15 (23.8) | 13 (21.6) | 6 (21.4) | 4 (16) | 8 (33.3) | 10 (22.2) | 2 (50) |
| Serious 16-24 | 4 (16) | 16 (25.3) | 12 (20) | 8 (28.6) | 4 (16) | 4 (16.7) | 7 (15.6) | 1 (25) |
| Severe 25-49 | 1 (4) | 17 (26.9) | 7 (11.7) | 11 (39.3) | 1 (4) | 2 (8.3) | 3 (6.7) | — |
| Critical 50-74 | 0 (0) | 1 (1.6) | 1 (1.7) | 0 (0) | 0 (0) | 0 (0) | — | — |
| Maximum 75 | 0 (0) | 1 (1.6) | 0 (0) | 1 (3.6) | 0 (0) | 0 (0) | — | — |
| Severity, n (%) | | | | | | | | |
| Very mild 1 | 1 (4) | 0 (0) | 1 (1.7) | 0 (0) | 1 (4) | 0 (0) | 1 (2.2) | |
| Mild 2 | 23 (92) | 27 (42.9) | 45 (75) | 5 (17.9) | 23 (92) | 18 (75) | 39 (8.7) | 2 (50) |
| Moderate 3 | 0 (0) | 12 (19.1) | 7 (11.7) | 5 (17.9) | 0 (0) | 4 (16.6) | 3 (6.7) | 1 (25) |
| Severe 4 | 1 (4) | 10 (15.9) | 5 (8.2) | 6 (21.4) | 1 (4) | 1 (4.2) | 1 (2.2) | 1 (25) |
| Very severe 5 | 0 (0) | 12 (19.1) | 1 (1.7) | 11 (39.3) | 0 (0) | 0 (0) | — | — |
| Unknown | — | 2 (3.1) | 1 (1.7) | 1 (3.6) | 0 (0) | 1 (4.2) | 1 (2.2) | — |
| GCS, n (%) | | | | | | | | |
| Mild 13-15 | 25 (100) | 24 (38.1) | 45 (75) | 4 (14.2) | 25 (100) | 24 (100) | 45 (100) | 4 (100) |
| Moderate 9-12 | 0 (0) | 24 (38.1) | 12 (20) | 12 (42.9) | 0 (0) | 0 (0) | | |
| Severe 3-8 | 0 (0) | 15 (23.8) | 3 (5) | 12 (42.9) | 0 (0) | 0 (0) | | |

*SD Standard Deviation

2. Favorable Outcome—Patients with mTBI

The five proteins H-FABP, IL-10, S100B, NF-L and GFAP were first evaluated for their individual capacities to predict outcome in patients with mTBI. All protein blood levels trend to be higher in patients with unfavorable outcome (GOSE≤4, n=4) compared to those with favorable outcome (GOSE≥5, n=45) (p=n.s). The ability of each biomarker for the detection of favorable outcome was afterwards evaluated when the protein reached 95-100% sensitivity. The best individually performing protein was S100B with a sensitivity of 100% and a specificity of 44% (Table 2).

TABLE 2

| Single-protein performance to differentiate between favorable (GOSE 5-8) and unfavorable (GOSE 1-4) outcome in mTBI patients | | | | |
| --- | --- | --- | --- | --- |
| | % pAUC (95% CI) | Threshold | % SP (95% CI) | 95-100% SE (95% CI) |
| IL10 | 1.2 (0.7-3.9) | 0.22 | 24.4 (13.3-37.8) | 100 (100-100) |
| HFABP | 1.1 (0.6-4.4) | 3.82 | 22.2 (11.1-35.6) | 100 (100-100) |
| GFAP | 0.7 (0.2-3.4) | 145.1 | 13.3 (4.4-24.4) | 100 (100-100) |
| NFL | 0.9 (0.4-4.9) | 6.25 | 17.8 (6.7-31.1) | 100 (100-100) |
| S100β | 2.2 (1.6-4.7) | 86.8 | 44.4 (31.1-57.8) | 100 (100-100) |

Biomarkers are shown according to their specificity obtained at 95-100% sensitivity; pAUC: partial area under the curve; SP: specificity; SE: sensitivity; All threshold concentrations are in pg/mL except for H-FABP which is in ng/mL.

Next, the proteins were analyzed together in panels including clinical parameters. The individual outcome prediction capacities of clinical parameters are presented in Table 3.

TABLE 3

Clinical parameters performances to differentiate between favorable (GOSE 5-8) and unfavorable (GOSE 1-4) outcome in mTBI patients.

| | % pAUC (95% CI) | Thresh-old | % SP (95% CI) | 95-100% SE (95% CI) |
|---|---|---|---|---|
| Age | 1.6 (1-3.8) | 27.5 | 31.1 (17.8-44.4) | 100 (100-100) |
| Marshall grade | 3.1 (2.5-3.8) | 1.5 | 62.2 (46.7-77.8) | 100 (100-100) |
| Severity | 0.3 (0.1-4.7) | 1.5 | 2.3 (0.0-6.8) | 100 (100-100) |

TABLE 3-continued

Clinical parameters performances to differentiate between favorable (GOSE 5-8) and unfavorable (GOSE 1-4) outcome in mTBI patients.

| | % pAUC (95% CI) | Thresh-old | % SP (95% CI) | 95-100% SE (95% CI) |
|---|---|---|---|---|
| ISS | 2.4 (1.7-3.8) | 5.5 | 46.7 (31.1-60) | 100 (100-100) |
| GCS | 0.2 (0.1-3.6) | Inf | 0.0 (0-0) | 100 (100-100) |

SP: specificity; SE: sensitivity. ISS: injury severity score. Severity was classified using an aggregate covariate combining the lowest Glasgow Coma Scale (GCS) before possible intubation and the length of posttraumatic amnesia The best combination using two proteins was IL-10 and S100B. This panel yielded sensitivity of 100% and a specificity of 62%. This combination increased the specificity with 18 percentage points compared to the best single molecule S100B. The best performing panel of three proteins included IL-10, H-FABP and S100B and had a sensitivity of 100% and a specificity increased up to 73% (Table 4).

TABLE 4

Panels performed in mTBI patients with two or three protein combinations using the individually significantly different proteins; H-FABP, 1L-10 and S100B.

| Outcome | Markers (cut-off) | n good outcome | n poor outcome | Panel cut-off | % SP (95% CI) | % SE (95% CI) |
|---|---|---|---|---|---|---|
| GOSE ≥ 5 vs GOSE ≤ 4 | IL-10 (0.219) S100 B (87.75) | 45 | 4 | 2 | 62.2 (48.9-77.8) | 100 (100-100) |
| | IL-10 (0.219) S100B (87.75) HFABP (3.81) | 45 | 4 | 3 | 73.3 (60-86.7) | 100 (100-100) |

Favorable outcome GOSE≥5 and unfavorable outcome GOSE≤4; SP: specificity; SE: sensitivity. All protein cut-off concentrations are in pg/mL except for H-FABP, which is in ng/mL.

The combination of individual proteins with clinical parameters recorded upon admission improved the predictive ability compared to biomarkers used in isolation. Combining S100B with patient's age and ISS reached a specificity of 89% with 100% sensitivity, which produces an increase in the specificity of 44 percentage points when comparing with the best single protein marker. The two-parameter panel including S100B and Marshall grade yielded a lower specificity (80%) (Table 5).

TABLE 5

Panels performed in mTBI patients including individually significantly different proteins; S100B and clinical parameters: Marshall grade severity, injury severity score, age.

| Outcome | Markers (cut-off) | n good outcome | n poor outcome | Panel cut-off | % SP (95% CI) | % SE (95% CI) |
|---|---|---|---|---|---|---|
| GOSE ≥ 5 vs GOSE ≤ 4 | S100B (86.82) Marshall (1-5) | 45 | 4 | 2 | 79.5 (68.2-90.9) | 100 (100-100) |
| | S100B (87.75) Age (27.5) ISS (5.5) | 45 | 4 | 3 | 88.6 (79.5-97.7) | 100 (100-100) |

Favorable outcome GOSE≥5 and unfavorable outcome GOSE≤4; SP: specificity; SE: sensitivity. All protein cut-off concentrations are in pg/mL except for H-FABP, which is in ng/mL.

3. Complete Recovery

H-FABP, IL-10, S100B, NF-L and GFAP were further investigated for their individual capacities to predict complete recovery in patients with mTBI. All protein blood levels trend to be higher in patients with incomplete recovery (GOSE≤7, n=24) compared to those with complete recovery (GOSE=8, n=25) (p=n.s). As in the case of favorable outcome prediction, the proteins were investigated when the sensitivity was set at 95-100%. Compared to previous analysis, the specificities remained low. The best performing protein was H-FABP, reaching 4% specificity and 100% sensitivity. NF-L and S100B had higher specificities of 12%, but lower sensitivities of 96% (Table 6).

TABLE 6

Single protein's performance to differentiate between complete (GOSE 8) and incomplete (GOSE ≤ 7) recovery in mTBI patients.

| | % pAUC (95% CI) | Threshold | % SP (95% CI) | 95-100% SE (95% CI) |
|---|---|---|---|---|
| IL10 | 0.0 (0.0-0.7) | Inf. | 0.0 (0-0) | 100 (100-100) |
| HFABP | 0.2 (0.0-0.7) | 44.9 | 4.0 (0.0-12) | 100 (100-100) |
| GFAP | 0.0 (0.0-0.6) | Inf. | 0.0 (0-0) | 100 (100-100) |

TABLE 6-continued

Single protein's performance to differentiate between complete (GOSE 8) and incomplete (GOSE ≤ 7) recovery in mTBI patients.

| | % pAUC (95% CI) | Threshold | % SP (95% CI) | 95-100% SE (95% CI) |
|---|---|---|---|---|
| NFL | 0.1 (0.0-1.2) | 4.85 | 12 (0.0-24.1) | 95.8 (87.5-100) |
| S100B | 0.1 (0.0-1.0) | 23.17 | 12 (0.0-28.0) | 95.8 (87.5-100) |

Biomarkers are shown according to their specificity obtained at 95-100% sensitivity. pAUC: partial area under the curve; SP: specificity; SE: sensitivity; All threshold concentrations are in pg/mL except for H-FABP which is in ng/mL.

Next, combinations of proteins to increase the ability to predict complete recovery were evaluated. The best two-protein panel was a combination of H-FABP and NF-L, reaching a specificity of 40% and sensitivity of 96% thus with a 36-percentage point increase in specificity compared to the best performing single protein H-FABP. A panel comprising three proteins: H-FABP, GFAP and NF-L, was further capable of increasing the specificity to 44% with 96% sensitivity (Table 7).

TABLE 7

Panels performed in mTBI patients with two or three protein combinations using the individually significantly different proteins; H-FABP, GFAP and NF-L.

| Outcome | Markers (cut-off) | n good outcome | n poor outcome | Panel cut-off | % SP (95% CI) | % SE (95% CI) |
|---|---|---|---|---|---|---|
| GOSE 8 vs GOSE ≤ 7 | H-FABP (6.26) NFL (15.9) | 25 | 24 | 1 | 40.0 (20.0-60.0) | 95.8 (87.5-100) |
| | H-FABP (5.01) NFL (13.46) GFAP (2457.5) | 25 | 24 | 1 | 44.0 (24.0-64.0) | 95.8 (87.5-100) |

Complete recovery GOSE 8 and incomplete recovery GOSE≤7; SP: specificity; SE: sensitivity. All protein cut-off concentrations are in pg/mL except for H-FABP, which is in ng/mL.

Combining individual proteins with clinical parameters was also evaluated to predict complete recovery (Table 8).

Combination of H-FABP, the most specific molecule in isolation, with clinical parameters showed the capacity of clinical parameters to improve the performance of proteins. Maintaining a value of 96% sensitivity, the combination of H-FABP, NF-L and TBI severity reached a specificity value of 56%. The individual outcome prediction capacities of clinical parameters are presented in Table 9.

TABLE 8

Panels performed in mTBI patients including individually significantly different proteins; H-FABP and NF-L and clinical parameter severity.

| Outcome | Markers (cut-off) | n good outcome | n poor outcome | Panel cut-off | % SP (95% CI) | % SE (95% CI) |
|---|---|---|---|---|---|---|
| GOSE 8 vs GOSE ≤ 7 | H-FABP (6.26) NFL (15.9) | 25 | 24 | 1 | 40.0 (20.0-60.0) | 95.7 (87.0-100) |
| | H-FABP (4.30) NFL (13.46) Severity (2.5) | 25 | 24 | 1 | 56.0 (36.0-76.0) | 95.7 (87.0-100) |

Complete recovery GOSE 8 and incomplete recovery GOSE 7; SP: specificity; SE: sensitivity. All protein cut-off concentrations are in pg/mL except for H-FABP, which is in ng/mL.

TABLE 9

| Clinical parameters performances to differentiate between complete (GOSE 8) and incomplete (GOSE ≤ 7) recovery patients in mTBI patients. | | | | |
|---|---|---|---|---|
| | % pAUC (95% CI) | Thresh-old | % SP (95% CI) | 95-100% SE (95% CI) |
| Age | 0.0 (0.0-2.0) | Inf. | 0.0 (0-0) | 100 (100-100) |
| Marshall grade | 0.2 (0.1-0.3) | Inf. | 0.0 (0-0) | 100 (100-100) |
| Severity | 0.3 (0.1-0.8) | 1.5 | 4.0 (0.0-12.0) | 100 (100-100) |
| ISS | 0.0 (0.0-1.2) | Inf. | 0.0 (0-0) | 100 (100-100) |
| GCS | 0.4 (0.1-0.9) | 13.5 | 4.0 (0-0-12.0) | 100 (100-100) |

SP: specificity; SE: sensitivity. ISS: injury severity score. Severity was classified using an aggregate covariate combining the lowest Glasgow Coma Scale (GCS) before possible intubation and the length of posttraumatic amnesia.

2.4. Favorable Outcome—Patients with TBIs of all Severities

H-FABP, IL-10, S100B, NF-L and GFAP were first evaluated for their individual capacities to predict outcome in patients with TBIs of all severities. All protein blood levels were significantly higher in patients with unfavorable outcome (GOSE≤4, n=28) compared to those with favorable outcome (GOSE≥5, n=60) (p≤0.001). The ability of each biomarker for the detection of favorable outcome was evaluated when the protein reached 95-100% sensitivity. According to these criteria, the best performing protein was IL-10, with a sensitivity reaching 96% and specificity of 50%. The proteins H-FABP and GFAP showed similar results, where the sensitivity was 96% for both and specificity of 30% and 28%, respectively (Table 10).

TABLE 10

| Single proteins' performance to differentiate between favorable (GOSE 5-8) and unfavorable (GOSE 1-4) outcome. | | | | |
|---|---|---|---|---|
| | % pAUC (95% CI) | Thresh-old | % SP (95% CI) | 95-100% SE (95% CI) |
| IL10 | 1.4 (0.7-3.0) | 0.388 | 50.0 (36.7-63.3) | 96.4 (89.3-100) |
| HFABP | 1.1 (0.6-2.7) | 4.305 | 30.0 (18.3-41.7) | 96.4 (89.3-100) |
| GFAP | 0.8 (0.3-2.3) | 415 | 28.3 (16.7-40.0) | 96.4 (89.3-100) |

TABLE 10-continued

| Single proteins' performance to differentiate between favorable (GOSE 5-8) and unfavorable (GOSE 1-4) outcome. | | | | |
|---|---|---|---|---|
| | % pAUC (95% CI) | Thresh-old | % SP (95% CI) | 95-100% SE (95% CI) |
| NFL | 0.5 (0.2-4.4) | 5.471 | 10.0 (3.3-18.3) | 100 (100-100) |
| S100B | 0.1 (0-1.4) | 23.174 | 6.7 (1.7-13.3) | 96.4 (89.3-100) |

Biomarkers are shown in order according to their specificity obtained at 95-100% sensitivity. pAUC: partial area under the curve; SP: specificity; SE: sensitivity; All threshold concentrations are in pg/mL except for H-FABP, which is in ng/mL.

The proteins performances were also evaluated when they were combined together in panels and when they were combined with clinical parameters; individual performances of clinical parameters are presented in Table 11.

TABLE 11

| Clinical parameters performances to differentiate between favorable (GOSE 5-8) and unfavorable (GOSE 1-4) outcome patients. | | | | |
|---|---|---|---|---|
| | % pAUC (95% CI) | Thresh-old | % SP (95% CI) | 95-100% SE (95% CI) |
| Age | 0.3 (0.1-1.9) | 20.5 | 8.3 (1.7-16.7) | 96.4 (89.3-100) |
| Marshall grade | 0.9 (0.4-3.2) | Inf. | 0 (0-0) | 100 (100-100) |
| Severity | 0.6 (0.3-1.6) | 1.5 | 1.7 (0-5.1) | 100 (100-100) |
| ISS | 0.6 (0.0-2.8) | 5.5 | 36.7 (25-50) | 96.4 (89.3-100) |
| GCS | 0.4 (0.2-1.2) | Inf. | 0 (0-0) | 100 (100-100) |

SP: specificity; SE: sensitivity. ISS: injury severity score. Severity was classified using an aggregate covariate combining the lowest Glasgow Coma Scale (GCS) before possible intubation and the length of posttraumatic amnesia The best combination using two proteins was IL-10 and H-FABP. This panel could reach 96% sensitivity and 58% specificity. This combination increased the specificity with 8 percentage points compared to the best single molecule IL-10. The best performing panel combining three proteins included IL-10, H-FABP and GFAP. This panel managed to maintain the sensitivity at 96% and to increase the specificity up to 63% (Table 12).

TABLE 12

| Panels with two or three protein combinations using the individually significantly different proteins; H-FABP, IL-10, GFAP, S100B and NF-L. | | | | | | |
|---|---|---|---|---|---|---|
| Outcome | Markers (cut-off) | n good outcome | n poor outcome | Panel cut-off | % SP (95% CI) | % SE (95% CI) |
| GOSE ≥ 5 vs GOSE ≤ 4 | IL-10 (0.388) H-FABP (4.305) | 60 | 28 | 2 | 58.3 (45.0-71.7) | 96.4 (89.3-100) |
| | IL-10 (0.388) H-FABP (4.305) GFAP (145.139) | 60 | 28 | 3 | 63.3 (51.7-75.0) | 96.4 (89.3-100) |

Favorable outcome GOSE≥5 and unfavorable outcome GOSE≤4; SP: specificity; SE: sensitivity. All protein cut-off concentrations are in pg/mL except for H-FABP, which is in ng/mL.

The combination of individual proteins with clinical parameters improved the predictive ability compared to predictions using only biomarkers. Combining IL-10 with patient age and TBI severity reached a value of 80% specificity for 96% sensitivity (Table 13).

TABLE 13

| | | | | | | |
|---|---|---|---|---|---|---|
| Panels including individually significantly different proteins; 1L-10 and NF-L and clinical parameters: severity and age. | | | | | | |
| Outcome | Markers (cut-off) | n good outcome | n poor outcome | Panel cut-off | % SP (95% CI) | % SE (95% CI) |
| GOSE ≥ 5 vs GOSE ≤ 4 | NFL (41.5) Severity (2.5) | 59 | 27 | 0.5 | 72.9 (61-84.7) | 96.3 (88.9-100) |
| | IL-10 (0.44) Age (61) Severity (2-5) | 59 | 27 | 2 | 79.7 (69.5-89.8) | 96.3 (88.9-100) |

Favorable outcome GOSE≥5 and unfavorable outcome GOSE≤4; SP: specificity; SE: sensitivity. All protein cut-off concentrations are in pg/mL except for H-FABP, which is in ng/mL.

2.5. Complete Recovery—Patients with TBIs of all Severities

The five proteins were further investigated for their individual capacities to predict complete recovery after a TBIs of all severities. All protein blood levels were significantly increased in patients with incomplete recovery (GOSE≤7, n=63) compared to complete recovery (GOSE=8, n=25) (p<0.05). The proteins were investigated when the sensitivity was set at 95-100%. The best performing protein was H-FABP, reaching 28% specificity and 97% sensitivity. The four proteins NF-L, S100B, IL-10 and GFAP all reached 12% specificity and sensitivity between 95-98% (Table 14 and 15).

TABLE 14

| | | | | |
|---|---|---|---|---|
| Single protein's performance to differentiate between complete (GOSE 8) and incomplete (GOSE ≤ 7) recovery. | | | | |
| | % pAUC (95% CI) | Thresh-old | % SP (95% CI) | 95-100% SE (95% CI) |
| IL10 | 0.2 (0.0-1.1) | 0.192 | 12.0 (0.0-24.0) | 95.2 (88.9-100) |
| HFABP | 0.8 (0.1-1.9) | 3.469 | 28.0 (12.0-44.0) | 96.8 (92.1-100) |
| GFAP | 0.0 (0.0-1.4) | 145.139 | 12.0 (0.0-28.0) | 95.2 (88.9-100) |
| NFL | 0.4 (0.0-1.2) | 4.852 | 12.0 (0.0-24.1) | 98.4 (95.2-100) |
| S100B | 0.3 (0.0-1.0) | 23.174 | 12.0 (0.0-28.0) | 96.8 (92.1-100) |

Biomarkers are shown in order according to their specificity obtained at 95-100% sensitivity. pAUC: partial area under the curve; SP: specificity; SE: sensitivity. All threshold concentrations are in pg/mL except for H-FABP which is in ng/mL.

TABLE 15

| | | | | |
|---|---|---|---|---|
| Clinical parameters performances to differentiate between complete (GOSE 8) and incomplete (GOSE ≤ 7) recovery patients. | | | | |
| | % pAUC (95% CI) | Thresh-old | % SP (95% CI) | 95-100% SE (95% CI) |
| Age | 0.2 (0.0-1.3) | 20.5 | 12 (0-24) | 95.2 (88.9-100) |
| Marshall grade | 0.3 (0.2-0.5) | Inf. | 0 (0-0) | 100 (100-100) |
| Severity | 0.5 (0.2-0.9) | 1.5 | 4 (0-12) | 100 (100-100) |
| ISS | 0.0 (0.0-1.4) | Inf. | 0 (0-0) | 100 (100-100) |
| GCS | 0.2 (0.1-0.3) | Inf. | 0 (0-0) | 100 (100-100) |

SP: specificity; SE: sensitivity. ISS: injury severity score. Severity was classified using an aggregate covariate combining the lowest Glasgow Coma Scale (GCS) before possible intubation and the length of posttraumatic amnesia.

Combinations of proteins to increase the ability to predict complete recovery were evaluated. The best two-protein panel was a combination of H-FABP and GFAP, reaching a sensitivity of 95% and specificity of 36%, thus with an 8-percentage point or 28.57% increase in specificity compared to the best performing single protein. A panel comprising three proteins: H-FABP, GFAP and S100B, was further capable of increasing the specificity to 48% with 95% sensitivity (Table 16).

TABLE16

| | | | | | | |
|---|---|---|---|---|---|---|
| Panels with two or three protein combinations using the individually significantly different proteins; H-FABP, IL-10, GFAP, S100B and NF-L. | | | | | | |
| Outcome | Markers (cut-off) | n good outcome | n poor outcome | Panel cut-off | % SP (95% CI) | % SE (95% CI) |
| GOSE 8 vs GOSE ≤ 7 | H-FABP (3.469) GFAP (145.139) | 25 | 63 | 2 | 36.0 (16.0-56.0) | 95.2 (88.9-100) |
| | H-FABP (3.469) GFAP (209.620) S100B (229.782) | 25 | 63 | 2 | 48.0 (28.0-68.0) | 95.2 (88.9-100 |

Complete recovery GOSE 8 and incomplete recovery GOSE≤7; SP: specificity; SE: sensitivity. All protein cut-off concentrations are in pg/mL except for H-FABP, which is in ng/mL Combining individual proteins with clinical parameters was also evaluated to predict complete recovery. Combination of H-FABP, the most specific molecule, with clinical parameters showed the capacity of clinical parameters to improve the performance of proteins. Maintaining a value of 95% sensitivity, the combination of H-FABP, patient age and TBI severity reached a specificity value of 52% (Table 17).

TABLE 17

| Outcome | Markers (cut-off) | n good outcome | n poor outcome | Panel cut-off | % SP (95% CI) | % SE (95% CI) |
|---|---|---|---|---|---|---|
| | Panels including individually significantly different proteins; H-FABP, IL-10, GFAP, S100B and NF-L and clinical parameters: severity and age. | | | | | |
| GOSE 8 vs GOSE ≤ 7 | IL-10 (0.44) Age (30.5) | 25 | 61 | 0.5 | 44 (24-64) | 96.7 (91.8-100) |
| | H-FABP(34.91) Age (30.5) Severity (2.5) | 25 | 61 | 1 | 52 (32-72) | |

Complete recovery GOSE 8 and incomplete recovery GOSE≤7; SP: specificity; SE: sensitivity. All protein cut-off concentrations are in pg/mL except for H-FABP, which is in ng/mL.

The invention claimed is:

1. A method for treating a subject having experienced a mild traumatic brain injury (TBI) comprising the steps of:
   a) determining the levels of IL-10 and H-FABP in one or more samples of the subject;
   b) comparing each level obtained under step a) with a corresponding reference value to determine an unfavorable recovery outcome, wherein the unfavorable recovery outcome is characterized by a level of IL-10>0.388 pg/mL and a level of H-FABP>4.305 ng/mL in the one or more samples of the subject; and
   c) treating the subject having the unfavorable recovery outcome under step b) with a neuroprotective agent or hypothermia;
wherein the unfavorable recovery outcome under step b) is assessed by a score of four (4) or less in accordance with the Glasgow Outcome Scale Extended (GOSE);
and wherein the method is performed on the one or more samples which are taken, independently, less than 24 hours after occurrence of the mild TBI.

2. The method according to claim 1, wherein the neuroprotective agent is selected from the group consisting of AC-11, acetyl-L-carnitine, acetylcholinerase inhibitors, acetylcysteine, an anti-protein-aggregation agent, simvastatin, growth hormone, rosuvastatin, statins, marijuana, β-blockers, enzogenol, cerebrolysin, nitric oxide synthase inhibitor, progesterone, ethanol, barbiturates, and erythropoietin.

3. The method of claim 1, further comprising in step a) determining a level of GFAP in addition to the levels of IL-10 and H-FABP in the one or more samples of the subject.

4. The method of claim 1, further comprising in step a) determining a level of S100B in addition to the levels of IL-10 and H-FABP in the one or more samples of the subject.

5. The method of claim 1, wherein the levels of IL-10 and H-FABP obtained under step a) are combined with one or more parameters comprising age, sex, Glasgow Coma Scale (GCS), Marshall classification of traumatic brain injury, Abbreviated Injury Score (AIS) and Injury Severity Score (ISS), and/or with one or more results from diagnostic methods comprising Computerized Tomography (CT) scan and Magnetic Resonance Imaging (MRI) to determine the unfavorable recovery outcome.

6. The method of claim 5, wherein the levels of IL-10 and H-FABP obtained under step a) are combined with one or more parameters comprising age, Marshall classification of traumatic brain injury, ISS and/or GCS to determine the unfavorable recovery outcome.

7. The method of claim 1, wherein the one or more samples are blood, plasma, urine, saliva, tears (lachrymal fluid) or cerebrospinal fluid (CSF).

8. The method of claim 1, wherein the one or more samples are blood.

9. The method of claim 1, wherein the method is characterized by a sensitivity of more than 90%, more than 95%, 96% or 97% or of 100% and a specificity of more than 40%, or at least 50%, or a sensitivity of more than 95% and a specificity of at least 25%, or 28%, or 36%.

10. The method of claim 1, wherein the method is characterized by a specificity of more than 90%, more than 95%, 96% or 97% or of 100% and a sensitivity of at least 50%.

11. The method of claim 10, wherein the method is characterized by a sensitivity of at least 58%, 60%, 65%, or 70%.

* * * * *